United States Patent [19]

Sircar

[11] 4,397,852

[45] Aug. 9, 1983

[54] [3,6-PYRIDAZINEDIYLBIS(THIO)]BIS-[2,2-DIMETHYLALKANOIC ACIDS] AND DERIVATIVES AS ANTI-ARTERIOSCLEROTIC AGENTS AND METHOD

[75] Inventor: Ila Sircar, Ann Arbor, Mich.

[73] Assignee: Warner-Lambert Company, Morris Plains, N.J.

[21] Appl. No.: 332,058

[22] Filed: Dec. 18, 1981

[51] Int. Cl.$^3$ .................... C07D 237/18; A61K 31/50
[52] U.S. Cl. ..................................... 424/250; 544/240
[58] Field of Search ................. 544/239, 240; 424/250

[56] References Cited

FOREIGN PATENT DOCUMENTS 1098000  1/1961  Austria ................................ 544/240
1099544  2/1961  Austria ................................ 544/240

OTHER PUBLICATIONS

Nawrocki and Uhlendorf, "Effects of Gemfibrozil", *Artery I*:303–313 (1978).

*Primary Examiner*—Donald G. Daus
*Assistant Examiner*—G. Hendricks
*Attorney, Agent, or Firm*—Ronald A. Daignault

[57] ABSTRACT

New substituted [3,6-pyridazinediylbis(thio)]bis-[2,2-dimethylalkanoic acids] and derivatives which are useful as anti-arteriosclerotic agents are disclosed. These compounds elevate the high density lipoprotein fraction of cholesterol, and also lower the low density lipoprotein fraction of cholesterol.

10 Claims, No Drawings

[3,6-PYRIDAZINEDIYLBIS(THIO)]BIS-[2,2-DIMETHYLALKANOIC ACIDS] AND DERIVATIVES AS ANTI-ARTERIOSCLEROTIC AGENTS AND METHOD

BACKGROUND OF THE INVENTION

Elevated levels of blood cholesterol and blood lipids are conditions which are believed related to the onset of arteriosclerosis. Thus, compounds capable of reducing the levels of these blood constituents are recognized as potentially useful anti-arteriosclerotic agents.

The compounds of the present invention are useful as anti-arteriosclerotic agents and are capable of elevating the high density lipoprotein fraction of cholesterol (HDL-cholesterol), which effect is known to lower the risk factor of coronary heart disease (Gordon, T. et al., High Density Lipoprotein as a Protective Factor Against Coronary Heart Disease, May 1977, The American Journal of Medicine, Vol. 62, pp. 707–714). Certain compounds of the invention also are able to reduce the low density lipoprotein fraction of cholesterol (LDL-cholesterol), thus further reducing the risk factor of coronary heart disease.

SUMMARY OF THE INVENTION

The invention sought to be patented in its generic chemical compound aspect is a compound having the structural formula I:

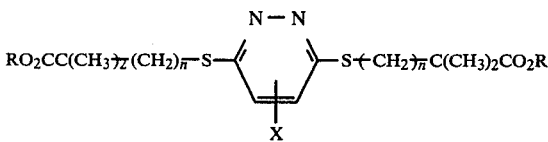

wherein n is an integer from 3–6, X is hydrogen, phenyl or alkyl of from 1 to 6 carbon atoms; R is hydrogen, alkyl of from 1 to 6 carbon atoms, or a pharmaceutically acceptable cation; and the pharmaceutically acceptable salts thereof.

The invention sought to be patented in a first subgeneric chemical compound aspect is a compound having the structural formula I wherein n is 3 and the pharmaceutically acceptable salts thereof.

The invention sought to be patented in a first generic chemical process aspect is a process for preparing a chemical compound having the structural formula I wherein n is an integer from 3–6; X is hydrogen, phenyl or alkyl of from 1 to 6 carbon atoms; R is hydrogen, alkyl of from 1 to 6 carbon atoms, or a pharmaceutically acceptable cation; which comprises reacting a substituted pyridazine of the structural formula II

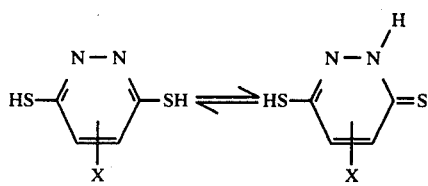

with 2 equivalents of a 2,2-dimethylalkanoic acid derivative having the structural formula III

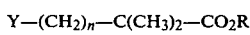

Y—(CH$_2$)$_n$—C(CH$_3$)$_2$—CO$_2$R    III wherein R, n and X are defined above, and Y is a halogen.

The invention sought to be patented in a second generic chemical process aspect is a process for preparing a compound having the structural formula I wherein n is an integer 3–6; X is hydrogen, phenyl or alkyl of from 1 to 6 carbon atoms; R is hydrogen, alkyl of from 1 to 6 carbon atoms, or a pharmaceutically acceptable cation; which comprises reacting a pyridazine having the structural formula IV

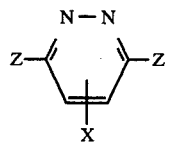

with 2 equivalents of a 2,2-dimethylalkanoic acid derivative having the structural formula V

HS(CH$_2$)$_n$C(CH$_3$)$_2$CO$_2$R    V wherein R, n and X are defined above, and Z is a halogen.

The invention sought to be patented in a pharmaceutical composition aspect is a composition useful for treating artereosclerosis in a mammal consisting essentially of a compound having the structural formula I or mixtures thereof, in combination with a pharmaceutically acceptable carrier.

The invention sought to be patented in a pharmaceutical method aspect is a method for treating arteriosclerosis in a mammal in need of such treatment; which comprises administering an effective amount of the above defined pharmaceutical composition to said mammal.

DESCRIPTION OF THE PREFERRED EMBODIMENTS

The compounds of the invention may be prepared by any of several processes which are to be considered as equivalent for purposes of this invention.

One such process involves the reaction between a pyridazine having the structural formula II,

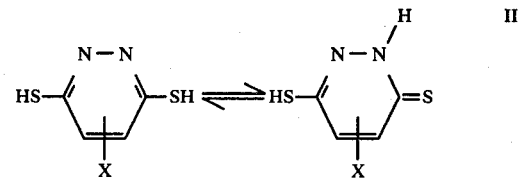

and two equivalents of a 2,2-dimethylalkanoic acid derivative having the structural formula III

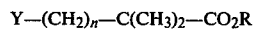

Y—(CH$_2$)$_n$—C(CH$_3$)$_2$—CO$_2$R    III wherein R, n and X are defined above, and Y is a halogen.

This reaction is most conveniently carried out in solution in a non-reactive solvent such as dimethoxyethane, dioxane, tetrahydrofuran, acetone, acetonitrile, dimethylsulfoxide or dimethylformamide at a temperature of up to about 120° C. in the presence of an acid acceptor such as a tertiary amine, pyridine or an alkali metal or alkaline earth metal carbonate or bicarbonate. In a preferred process, Y represents bromine and the above reaction is carried out in dimethylformamide solution at a temperature of about 60°-70° C. in the presence of potassium carbonate. In this preferred procedure, the reaction is substantially complete in about 6-8 hours. The carboxylic acid esters and acids of structural formula III may be prepared as described in U.S. Pat. No. 3,674,836 or by obvious variations thereof.

In a second process for preparing the compounds of the invention, a pyridazine of the structural formula IV

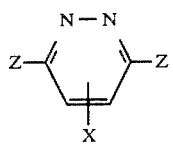

IV is reacted with 2 equivalents of a 2,2-dimethylalkanoic acid derivative having the structural formula V

$HS(CH_2)_nC(CH_3)_2CO_2R$  V wherein R, n and X are as defined above, and Z is a halogen.

The reaction between Compounds IV and V is carried out in a non-reactive solvent such as toluene or xylene in the presence of a strong base such as sodium hydride.

In a preferred procedure, compound V is first reacted with sodium hydride in toluene without the addition of external heating. Subsequently, a solution of IV in toluene is slowly added and the mixture is allowed to reflux overnight. The product is isolated and purified by standard procedures. In this preferred procedure, substituent Z represents chlorine. The compounds of formula IV may be prepared as described in Bull. Soc. Chim., 1004(1957).

The compounds of the invention of formula I wherein R is hydrogen form pharmaceutically acceptable salts with both organic and inorganic acids and bases. Examples of suitable acids for salt formation are hydrochloric, sulfuric, phosphoric, acetic, citric, oxalic, malonic, salicyclic, malic, fumaric, succinic, ascorbic, maleic, methansulfonic and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

Examples of suitable bases for salt formation are sodium hydroxide, sodium carbonate, sodium bicarbonate, potassium hydroxide, calcium hydroxide, ammonia, organic amines and the like. The salts are prepared by contacting the free acid form with an equivalent amount of the desired base in the conventional manner. The free acid forms may be regenerated by treating the salt form with an acid. For example, dilute aqueous acid solutions may be utilized. Dilute aqueous hydrochloric acid, sulfuric acid or acetic acid are suitable for this purpose. The free acid forms differ from their respective salt forms somewhat in certain physical properties such as solubility in polar solvents, but the salts are otherwise equivalent to their respective free acid forms for purposes of the invention.

The compound of the invention wherein R is alkyl of from 1 to 6 carbon atoms form pharmaceutically acceptable salts with both organic and inorganic acids. Examples of suitable acids and methods of preparation of the salts are identical to those given above.

The compounds of the invention can exist in unsolvated as well as solvated forms, including hydrated forms. In general, the solvated forms, with pharmaceutically acceptable solvents such as water, ethanol and the like are equivalent to the unsolvated forms for purposes of the invention.

The term halogen is intended to include chlorine, bromine and iodine.

The alkyl groups contemplated by the invention, unless specified otherwise, comprise both straight and branched carbon chains of from 1 to about 6 carbon atoms. Representative of such groups are methyl, ethyl, isopropyl, butyl, pentyl, 3-methylpentyl, and the like.

The compounds of the invention are new chemical substances of value as pharmacological agents for the treatment of arterosclerosis in warm-blooded animals. The anti-artereosclerotic activity of representative compounds of the invention was established by the Screening procedure described in Maxwell, R. E., Nawrocki, J. W., and Uhlendorf, P. D., Artery, 1, 303 (1978). This procedure is incorporated by reference herein. Utilizing this procedure at a dose level of 50 mg/kg, the following results were obtained for representative compounds of the invention. A compound is considered active if it increases the HDL cholesterol fraction by 50%.

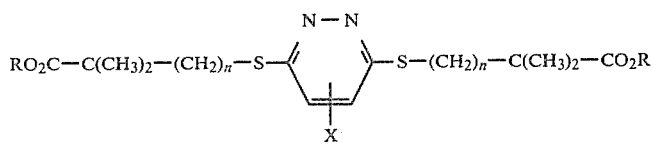

| R | X | n | % Change In Cholesterol | % Change In Triglyceride | % Change in HDL | % Change In LDL | % Change in Liver wt. |
|---|---|---|---|---|---|---|---|
| $CH_3$ | H | 3 | −24 | +166 | +1129 | −67 | +32 |
| $CH_3$ | $C_6H_5$ | 3 | −43 | 0 | +64 | −51 | 0 |
| $CH_3$ | $CH_3$ | 3 | 0 | +34 | +348 | −42 | +26 |
| $CH_3$ | H | 4 | −14 | +15 | +134 | −25 | +7 |

-continued

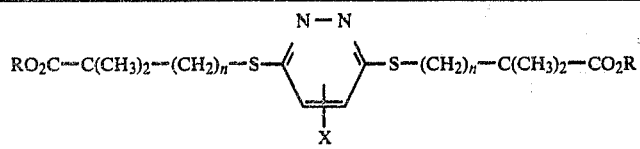

| R | X | n | % Change In Cholesterol | % Change In Triglyceride | % Change in HDL | % Change In LDL | % Change in Liver wt. |
|---|---|---|---|---|---|---|---|
| CH$_3$ | H | 6 | 0 | −26 | +33 | −17 | +8 |

An increase in liver weight is indicative of hepatomegaly and hepatic peroxisome proliferation. Both are undesirable side effects of the known anti-artereosclerotic agents, Reddy, J. F., and Krishnakantha, T. P., Science, 190, 787 (1975).

The compounds of the invention can be prepared and administered in a wide variety of oral and parenteral dosage forms. It will be clear to those skilled in the art that the following dosage forms may comprise as the active component, either a compound of formula I, or a corresponding pharmaceutically acceptable salt of a compound of formula I, or a mixture of such compounds and/or salts.

For preparing pharmaceutical compositions from the compounds described by this invention, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 to 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methyl cellulose, sodium carboxymethyl cellulose and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these packaged form.

The quantity of active compound in a unit dose of preparation may be varied or adjusted from 1 mg to 100 mg according to the particular application and the potency of the active ingredient.

In therapeutic use as agents for treating artereosclerosis, the compounds utilized in the pharmaceutical method of this invention are administered at the initial dosage of about 10 mg to about 500 mg per kilogram daily. A daily dose range of about 10 mg to about 250 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following non-limiting examples illustrate the inventor's preferred methods for preparing the compounds of the invention.

EXAMPLE 1

A mixture of 3-mercapto-6-(1H)-pyridazinethione (14.2 g, 0.1 mole) prepared according to A. Pollak, et. al., Canadian Journal of Chemistry, 44, 829 (1966), anhydrous K$_2$CO$_3$ (0.2 mole, 27.0 g) and methyl-5-bromo-2,2-dimethylpentanoate (0.23 mole, 56 mole) in dimethylformamide (300 ml) was stirred at 75°–80° C. for 13–14 hrs. The mixture was cooled, filtered from the inorganic salts, and dimethylformamide was distilled off under reduced pressure. The residue was distilled under vacuum to remove the excess bromoester and then chromatographed over silicagel. The product was eluted out with hexaneisopropylether (1:1) and then purified by crystallization from hexane to yield 26.0 g of the product, dimethyl-5,5'-[3,6-pyridazinediylbis(thio)]-bis[2,2-dimethylpentanoate] m.p. 32°–33° C.

Following the procedure of example 1, with the substitution of substituted pyridazines, the following additional products were obtained.

EXAMPLE 2

From 4-phenyl-3,6-dimercaptopyridazine, the product obtained is dimethyl-5,5'-[(4-phenyl-3,6-pyridazinediyl) bis(thio)]bis[2,2-dimethylpentanoate].

EXAMPLE 3

From 4-methyl-3,6-dimercaptopyridazine, (J. Druey, K. D. Meier and K. Eichenberger; Helv. Chim. Acta. 37, 121, 1954) the product obtained is dimethyl-5,5'-[(4-methyl-3,6-pyridazinediyl)bis(thio)]bis[2,2-dimethylpentanoate].

EXAMPLE 4

Following the procedure of Example 1, with the substitution of methyl 6-bromo-2,2-dimethylhexanoate in place of methyl 5-bromo-2,2-dimethylpentanoate, the product obtained is dimethyl 6,6'-[3,6-pyridazinediyl-bis(thio)]bis[2,2-dimethylhexanoate].

EXAMPLE 5

A solution of 1.07 g dimethyl 5,5'-[3,6-pyridazinediyl-bis(thio)]bis[2,2-dimethylpentanoate] in methanol (40 ml) was heated to reflux with a solution of NaOH (0.22 g) in water (10 ml) for 4 hours. Methanol was distilled off and the solution was acidified. Upon usual work up the product obtained is 5,5'-[3,6-pyridazinediylbis(thio)]bis[2,2-dimethylpentanoic acid], mp 112°–114° C. following crystallization from chloroform/pet ether.

PREPARATIVE EXAMPLE

3-Mercapto-4-phenyl-6(1H)-pyridazinethione

A mixture of phosphorous pentasulfide (15.0 g), 4-phenyl-3,6-pyridazinedione (2.5 g) in pyridine (38 ml) was refluxed for 3 hrs. Pyridine was distilled off and the residue was poured into water and the mixture was heated to boiling until complete dissolution took place. The solution was then made alkaline with sodium hydroxide followed by acidification. The solids were filtered, washed with water, and dried. The product obtained has mp. 146°–148° C., following crystallization from toluene.

I claim:

1. A compound having the structural formula

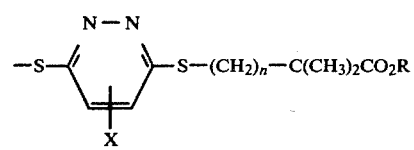

wherein n is 3; X is hydrogen, phenyl, or alkyl of from 1 to 6 carbon atoms; R is hydrogen, alkyl of from 1 to 6 carbon atoms or a pharmaceutically acceptable cation; and the pharmaceutically acceptable acid addition salts thereof.

2. The compounds defined in claim 1 wherein R is methyl, and the pharmaceutically acceptable acid addition salts thereof.

3. The compounds defined in claim 1 wherein R is hydrogen, an the pharmaceutically acceptable acid and base addition acids thereof.

4. The compound defined in claim 1 which is dimethyl 5,5'-[3,6-pyridazinediylbis(thio)]bis [2,2-dimethylpentanoate] and the pharmaceutically acceptable acid addition salts thereof.

5. The compound defined in claim 1 which is dimethyl 5,5'-[(4-phenyl-3,6-pyridazinediyl)bis(thio)]-bis[2,2-dimethylpentanoate] and the pharmaceutically acceptable acid addition salts thereof.

6. The compound defined in claim 1 which is dimethyl 5,5'-[(4-methyl-3,6-pyridazinediyl)bis(thio)]-bis[2,2-dimethylpentanoate] and the pharmaceutically acceptable acid addition salts thereof.

7. Dimethyl 6,6'-(3,6-pyridazinediylbis(thio)bis(2,2-dimethyl hexanoate) and the pharmaceutically acceptable acid addition salts thereof.

8. The compound defined in claim 1 which is 5,5'-[3,6-pyridazinediylbis(thio)]bis[2,2-dimethylpentanoic acid] and the pharmaceutically acceptable acid and base addition salts thereof.

9. A composition useful for treating artereosclerosis in a mammal consisting essentially of a compound defined in claim 1 or mixtures thereof, in combination with a pharmaceutically acceptable carrier.

10. A method for treating arteriosclerosis in a mammal in need of such treatment; which comprises administering an effective amount of the pharmaceutical composition defined in claim 9 to said mammal.

* * * * *